United States Patent [19]

Joensen et al.

[11] Patent Number: 5,728,871
[45] Date of Patent: Mar. 17, 1998

[54] PROCESS FOR THE PREPARATION OF ACETIC ACID

[75] Inventors: Finn Joensen, Hørsholm; Bodil Voss, Virum; Ib Dybkjær, Copenhagen, all of Denmark

[73] Assignee: Haldor Topsoe A/S, Lyngby, Denmark

[21] Appl. No.: 832,880

[22] Filed: Apr. 4, 1997

[30] Foreign Application Priority Data

Apr. 10, 1996 [DK] Denmark ................. 0407/96

[51] Int. Cl.$^6$ .................................................. C07C 51/12
[52] U.S. Cl. .................................................. 562/519
[58] Field of Search ...................................... 562/519

[56] References Cited

U.S. PATENT DOCUMENTS

| | | | |
|---|---|---|---|
| 3,769,329 | 10/1973 | Paulik et al. | 560/232 |
| 4,110,359 | 8/1978 | Marion | 518/703 |
| 5,189,203 | 2/1993 | Hansen et al. | 560/232 |
| 5,286,900 | 2/1994 | Hansen et al. | 560/232 |

FOREIGN PATENT DOCUMENTS

| | | |
|---|---|---|
| 0250189 | 12/1987 | European Pat. Off. . |
| 2206349 | 1/1989 | United Kingdom . |

Primary Examiner—Gary Geist
Assistant Examiner—Rosalynd Keys
Attorney, Agent, or Firm—Ostrolenk, Faber, Gerb & Soffen, LLP

[57] ABSTRACT

A process for the preparation of acetic acid by catalytic conversion of a synthesis gas being rich in hydrogen and carbon monoxide, comprising steps of:

(i) introducing a stream of the synthesis gas into a first reaction step at a predetermined pressure and temperature and reacting the synthesis gas in the presence of a catalyst being active in formation of methanol and dehydration of methanol, so as to obtain a gaseous process phase containing methanol, dimethyl ether, and water;

(ii) cooling the gaseous process phase of step (i) and obtaining a liquid phase with the methanol, dimethyl ether and water and a gaseous phase comprising carbon dioxide and residual amounts of dimethyl ether;

(iii) introducing the liquid phase formed in step (ii) into a second reaction step at a predetermined pressure and temperature and adding a predetermined amount of carbon monoxide; and (iv) carbonylating methanol and dimethyl ether in the liquid phase with carbon monoxide by contact with a catalyst being active in the carbonylation of alcohols and ethers with carbon monoxide; and (v) recovering from effluent of step (iv) a product stream mainly consisting of the acetic acid product.

5 Claims, No Drawings

PROCESS FOR THE PREPARATION OF ACETIC ACID

FIELD OF THE INVENTION

The present invention relates to preparation of acetic acid from a synthesis gas of hydrogen and carbon oxides. More particular, the invention comprises catalytical steps of converting hydrogen and carbon monoxide in the gas to a mixed process stream containing methanol and dimethyl ether (DME) and carbonylating methanol and DME formed in the process stream into acetic acid.

BACKGROUND OF THE INVENTION

The conventional process for the manufacture of acetic acid presently widely used in the industry includes catalytical carbonylation of methanol as disclosed by e.g. U.S. Pat. No. 3,769,329 and EP Patent No 250,189.

Catalysts usually employed in the carbonytation reaction comprise a rhodium compound promoted with methyl iodide.

The conventional acetic acid process, however, requires supply of methanol reactant from external sources.

To eliminate the need for external supply of methanol synthesis of methanol can be integrated into the acetic acid process by producing methanol and carbon monoxide in parallel.

Integration of methanol and carbon monoxide production is, in particular, convenient when both reactants are prepared from synthesis gas obtained at high efficiency through steam reforming of natural gas.

The major drawback in parallel production of methanol and carbon monoxide is, however, the reaction pressure required in the methanol synthesis, which in order to achieve acceptable conversion rates must be significantly higher than the pressure typically used in the subsequent acetic acid synthesis step.

The above problem with different synthesis pressure in the methanol and subsequent acetic acid synthesis is overcome by introduction of a combined methanol/dimethyl ether synthesis in the first reaction step of the acetic acid preparation process, as disclosed in U.S. Pat. Nos. 5,189,203 and 5,286,900, the entire disclosures of which is incorporated herein by reference.

Simultaneous preparation of methanol and DME from hydrogen and carbon oxides containing synthesis gas is catalyzed by a number of catalysts such as the known methanol catalyst including mixed oxides of Cu/Zn/Cr or Cu/Zn/Al and methanol dehydration catalysts such as alumina, silica-alumina, zeolitic materials, silica alumino phosphates and heteropoly acids of Mo and W being applied as physical mixture or prepared by co-impregnation on carrier materials, co-pelletization or co-precipitation.

In the process disclosed in the above U.S. patents combined methanol and DME synthesis is followed by carbonylation of methanol and DME to acetic acid products. An advantageous feature of these processes is that the simultaneous conversion of synthesis gas to methanol and DME may be performed at high conversion rate at a pressure substantially corresponding to the synthesis pressure in the subsequent acetic acid reaction step.

The above process requires excess of carbon monoxide in the feed gas for the methanol/DME synthesis in order to provide sufficient concentration of the carbon monoxide reactant in the effluent from the methanol/DME synthesis for the carbonylation reaction in the subsequent acetic acid synthesis. As a consequence of the CO concentration being in excess of the stoichiometric requirement in the methanol/DME synthesis, significant amounts of carbon dioxide are formed by the following reaction:

$$5CO + 3H_2 \rightarrow CH_3OCH_3 + 2CO + CO_2 \quad (1)$$

High carbon dioxide concentration in the effluent from the methanol/DME synthesis represents the major drawback of this process. Carbon dioxide acts essentially as an inert gas in the carbonylation reaction and, therefore, necessitates higher synthesis pressure in the acetic acid reaction step in order to maintain a sufficient pressure of carbon monoxide.

The general object of this invention is to provide improvements in the known process for the preparation of acetic acid from a hydrogen and carbon monoxide containing synthesis gas including synthesis of methanol and DME in a first catalytic reaction stage and subsequent carbonylation of methanol and DME recovered from the effluent of the first reaction stage.

SUMMARY OF THE INVENTION

A process for the preparation of acetic acid by catalytic conversion of a synthesis gas being rich in hydrogen and carbon monoxide, comprising steps of:

(i) introducing a stream of the synthesis gas into a first reaction step at a predetermined pressure and temperature and reacting the synthesis gas in the presence of a catalyst being active in formation of methanol and dehydration of methanol, so as to obtain a gaseous process phase containing methanol, dimethyl ether, and water;

(ii) cooling the gaseous process phase of step (i) and obtaining a liquid phase with the methanol, dimethyl ether and water and a gaseous phase comprising carbon dioxide and residual amounts of dimethyl ether;

(iii) introducing the liquid phase formed in step (ii) into a second reaction step at a predetermined pressure and temperature and adding a predetermined amount of carbon monoxide; and (iv) carbonylating methanol and dimethyl ether in the liquid phase with carbon monoxide by contact with a catalyst being active in the carbonylation of alcohols and ethers with carbon monoxide; and (v) recovering from effluent of step (iv) a product stream mainly consisting of the acetic acid product.

Carbon monoxide for use in the carbonylation step is readily available from many sources.

Carbon monoxide may be supplied from steam reformed natural gas or various offgases from chemical plants, steel production, etc. through membrane or cryogenic separation of the monoxide.

In accordance with another aspect of the invention carbon monoxide reactant is recovered directly from the feed gas to the first reaction step of the above process by dividing the feed gas stream into two substrates preferably with a volume ratio of between 0.5:1 and 2:1 of a first and second substrate. Carbon monoxide is then separated by conventional membrane or cryogenic separation methods from the second substrate of the feed gas.

Thus, in a further embodiment of the invention, the process comprises the further steps of:

prior to introducing the synthesis gas into the first reaction step dividing the gas into a first and second portion;

passing the first portion of the gas to step (i) of the process;

treating the second portion of the gas for recovery of carbon monoxide contained therein; and passing recovered amounts of the carbon monoxide to step (iv) of the process.

DETAILED DESCRIPTION OF THE INVENTION

As initially mentioned, the combined synthesis of methanol and DME is performed in presence of a catalytic system catalyzing the formation of methanol and dehydration of methanol to DME by the reactions:

$$CO+2H_2 \rightleftharpoons CH_3OH \qquad (2)$$

$$2CH_3OH \rightleftharpoons CH_3OCH_3+H_2O \qquad (3)$$

Those catalysts include the aforementioned catalysts and, in particular, catalysts with a composition of about 60 atom % Cu, 25 atom % Zn and 15 atom % Al being highly active in the methanol forming reaction (2) and alumina or alumina silicates for the DME reaction (3).

The catalysts in the first process step may be arranged in a fixed bed as an intimately mixture or as a layered bed with alternating methanol synthesis and methanol dehydration catalyst particles. Physical mixtures of the catalysts result in lower selectivity and it is preferred to employ a fixed bed of a catalyst composition with combined methanol, and methanol dehydration activity. Such a catalyst composition may be prepared by impregnation, copelletization or coprecipitation of the catalytic active materials in accordance with the known methods in the manufacture of catalysts.

Through contact with the above catalyst compositions hydrogen and carbon monoxide in the feed gas are by the above reactions (2) and (3) converted to methanol, DME and water. Produced water is shifted to carbon dioxide and hydrogen by the water gas shift reaction:

$$H_2O+CO \rightleftharpoons CO_2+H_2 \qquad (4),$$

proceeding simultaneously with reactions (2) and (3).

As discussed hereinbefore, the known acetic acid processes utilizing combined methanol/DME synthesis in a first reaction step require in the feed gas excess of carbon monoxide in relation to the stoichiometric requirement at the methanol forming reaction (2) in order to leave in the effluent from the methanol/DME reactions the necessary amount of carbon monoxide for the carbonylation of the reaction products in the subsequent acetic acid preparation step.

In contrast to the above processes, the process of this invention can be operated advantageously at a high hydrogen/carbon monoxide ratio in the feed gas to the methanol/DME reaction. The hydrogen/carbon monoxide ratio required in the feed gas is typically between 2:1 and 3:1, as supplied by unadjusted synthesis gas from conventional steam reforming of a hydrocarbon feedstock. Thereby, substantially all of the carbon monoxide in the feed gas is converted to DME and methanol and formation of inert carbon dioxide by-product is considerably reduced. Conversion levels similar to those of the conventional methanol synthesis are achieved at a synthesis pressure of 25–50 bar, which corresponds to the required pressure in the subsequent acetic acid reaction step.

Produced methanol, DME and water are recovered in the liquid phase from the effluent of the above reaction step by cooling the effluent and purging of a gaseous phase containing small amounts of unconverted feed gas and carbon dioxide.

Due to the high vapour pressure of DME, the purge gas further contains a part of produced DME. Therefore, it is preferred to subject the purge gas from the effluent to a purge wash with a suitable liquid washing agent, preferably methanol or acetic acid. DME recovered from the purge gas is then combined with the liquid phase.

In the final reaction step of the process, catalytic carbonylation of DME and methanol to acetic acid is carried out with carbon monoxide being supplied to the reaction as separate stream.

In the final step, carbon monoxide is added in an amount corresponding at least to the stoichiometric amount in the carbonylation reaction:

$$CH_3OH+CO \rightarrow CH_3COOH \qquad (5)$$

$$CH_3OCH_3+2CO+H_2O \rightarrow 2CH_3COOH \qquad (6)$$

Typically to provide sufficient amount of carbon monoxide, the carbon monoxide will be added in an amount providing a mole ratio of carbon monoxide and methanol plus DME, i.e.

$$CO/(CH_3OH+2CH_3OCH_3),$$

in the carbonylation reaction in the range of between 1 to 1.5.

As previously mentioned, a number of catalyst composition being active in the above carbonylation reactions are known in the art. Catalysts usually employed are based on a combination of Group VIII transition metal compounds and a halogen compound promoter. Additionally, a number of secondary promoters have been disclosed in the art, comprising metal salts, organo-N, organo-P and organo-S compounds.

Preferred catalysts for use in the process of the invention include compounds of group VIII metals of the Periodic System promoted with iodine or bromine compounds.

The carbonylation reaction may be carried out within a wide range of temperature from about 100° C. to 400° C., though a temperature between 100° C. and 250° C. is sufficient to obtain acceptable reaction conditions.

Preferably, the reaction is carried out in the liquid phase at elevated pressure by establishing a partial pressure of the carbon monoxide in the gas phase over the liquid reaction phase in the reactor being sufficiently high to provide sufficient concentration of dissolved carbon monoxide in the liquid phase for the carbonylation reactions proceeding in this phase. Sufficient pressure will be in the range of 25–50 bar depending on the reaction temperature and catalyst concentration. Carbon monoxide is usually introduced continuously at the bottom of the reactor and bubbled through the liquid process phase in an amount sufficient to reach the desired yield of acetic acid product in the carbonylation reactions as mentioned above.

As mentioned hereinbefore, carbon monoxide may be supplied from external sources or preferably from a substrate of the carbon monoxide containing feed gas by conventional separation methods, such as cryogenic separation or separation of the monoxide in a membrane unit, wherein hydrogen in the gas selectively permeates through a hollow fibre membrane and carbon monoxide is recovered in the residue stream of the membrane unit.

EXAMPLE 1

Preparation of acetic acid by carbonylation of a mixture containing methanol and DME in presence of a rhodium catalyst and a methyl iodide promoter.

A 600 ml Hastelloy C autoclave was charged with 120 g (2.00 mole) acetic acid, 10 g (0.31 mole) methanol, 38 g (2.11 mole) water, 24 g (0.17 mole) methyl iodide, together with 0.09 g (0.34 mmole) of rhodium chloride hydrate. The autoclave was sealed and purged with helium. 16 g (0.35 mole) DME were introduced through the autoclave inlet tube. The autoclave was heated to 185° C. under continuous stirring and pressurized to 36 bar with carbon monoxide. Temperature was maintained at 185° C. and the pressure was kept constant by continuous addition of carbon monoxide. After two hours the autoclave was cooled and depressurized and the resultant reaction mixture (234 g) was analyzed to yield the following distribution of products: 71.8 wt-% of acetic acid, 0.2 wt-% of methanol, 10.1 wt-% of methyl iodide and 4.1 wt-% of methyl acetate.

EXAMPLE 2

A pilot plant as schematically shown in FIG. 1 of the drawings for use in the preparation of acetic acid according to a specific embodiment of the invention comprises a synthesis step 100 for the preparation of a methanol MeOH-DME-water containing process stream, a membrane separation unit 102 for recovery of carbon monoxide step and an acetic acid synthesis step for manufacture of acetic acid by catalytic carbonylation of the process stream with carbon monoxide supplied by the effluent stream from the membrane unit.

In the pilot plant 3.9 $Nm^3/h$ of a synthesis gas stream 1 was converted in synthesis step 100 in presence of a catalyst consisting of a physical mixture of a conventional methanol Cu—Zn—Al catalyst (Haldor Topsøe MK-101) and a dehydration catalyst (La Roche Versal 250, calcined at 550° C. in air for 2 hours) in a ratio of 1:2 by weight, at a pressure of 39 bar and a temperature of between 240° C. and 290° C. From the reactor, a $DME/MeOH/H_2O$ containing process stream was withdrawn and cooled to 20° C. to obtain a gaseous stream and liquid stream 2. Liquid stream 2 was passed to acetic acid reactor 104.

A second stream of the process stream was passed to membrane unit 102 (Perma Prism®) for selective recovery of carbon monoxide contained in the process stream.

At a pressure of 39 bar and a temperature of 20° C. 96.6 mole % of carbon monoxide in the stream were recovered and passed in stream 3 to the acetic acid reactor 104. In the acetic acid reactor stream 2 and 3 were catalytically converted in the liquid phase to acetic acid product at a pressure of 36 bar and a temperature of 185° C. as described in detail herein before.

A liquid stream 4 containing the acetic acid product and gas stream 5 of mainly unreacted carbon monoxide were withdrawn from the reactor and depressurized to 0.6 bar g.

Both streams were introduced into a catalyst recovery unit 106, wherein amounts of catalyst being withdrawn together with stream 4 were separated and recycled together with part of liquid acetic acid product via line 6 and 2 to the acetic acid reactor 104. Residual amounts of acetic acid product were passed in the gas phase from top of unit 106 in line 7 to a distillation column 108 and subjected to distillation. A bottom product substantially consisting of acetic acid was withdrawn from unit 108 in product line 8. Stream 8 was divided into a product stream 16 of the acetic acid product and a washing stream 15 for use in a washing unit as further described below.

From top of unit 108, a gas stream 9 containing carbon monoxide, methyl iodide catalyst promoter and water was passed to a separator 110. In unit 110, the content of gas stream 9 was separated into a heavy liquid phase of mainly methyl iodide, a light liquid aqueous phase and the remaining gas phase of mainly carbon monoxide and some methyl iodide. Both liquid phases were recycled in line 10 and 11 and via line 2 to reactor 104.

The gaseous phase from unit 110 was passed in stream 12 to a purge gas washing unit 112, in which methyl iodide content was recovered by wash with acetic acid being supplied from the acetic acid product stream via line 15. Recovered amounts of methyl iodide were recycled together with acetic acid wash-stream in line 13 to distillation unit 108.

Composition and flow of the above mentioned streams are summarized in Table 1.

TABLE 1

|  | 1 | 2 | 3 | 4 | 5 | 6 | 7 | 8 | 12 | 15 | 16 |
|---|---|---|---|---|---|---|---|---|---|---|---|
| Flow Kg/h |  | 1.65 |  | 27.8 |  | 19.6 |  | 5.05 |  | 1.99 | 3.06 |
| Flow $Nm^{2/h}$ | 7.8 |  | 1.29 |  | 0.20 |  | 3.71 |  | 0.22 |  |  |
| $H_2$ Mole % | 66.0 | 0.1 | 1.5 | n.a. |  | n.a. |  | n.a. |  |  |  |
| $H_2O$ Mole % |  | 32.5 |  | 43.0 | n.a. | 39.9 | n.a. | 1.2 | n.a. | 1.2 | 1.2 |
| CO Mole % | 33.4 |  | 96.6 | n.a. | 68.2 |  | 3.1 |  | 59.6 |  |  |
| $CO_2$ Mole % | 0.6 | 1.3 | 1.9 | n.a. | 13.9 |  | 0.6 |  | 15.3 |  |  |
| MeOH Mole % |  | 31.8 |  |  |  |  |  |  |  |  |  |
| DME Mole % |  | 34.2 |  |  |  |  |  |  |  |  |  |
| HOAC Mole % |  |  |  | 50.6 | 0.1 | 57.5 | 32.7 | 98.8 |  | 98.8 | 98.8 |
| MeOAc Mole % |  |  |  | 0.9 | 0.1 | 0.7 | 1.7 |  |  |  |  |
| MeI Mole % |  |  |  | 5.1 | 0.4 | 1.3 | 13.4 |  | 11.8 |  |  | n.a.: not analyzed

We claim:

1. A process for the preparation of acetic acid by catalytic conversion of a synthesis gas being rich in hydrogen and carbon monoxide, comprising steps of:

(i) introducing a stream of the synthesis gas into a first reaction step at a predetermined pressure and temperature and reacting the synthesis gas in the presence of a catalyst being active in formation of methanol and dehydration of methanol, so as to obtain a gaseous process phase containing methanol, dimethyl ether, and water;

(ii) cooling the gaseous process phase of step (i) and obtaining a liquid phase with the methanol, dimethyl ether and water and a gaseous phase comprising carbon dioxide and residual amounts of dimethyl ether;

(iii) introducing the liquid phase formed in step (ii) into a second reaction step at a predetermined pressure and temperature and adding a predetermined amount of carbon monoxide; and (iv) carbonylating methanol and dimethyl ether in the liquid phase with carbon monoxide by contact with a catalyst being active in the carbonylation of alcohols and ethers with carbon monoxide; and (v) recovering from effluent of step (iv) a product stream mainly consisting of the acetic acid product.

2. The process of claim 1, comprising the further steps of:

prior to introducing the synthesis gas into the first reaction step dividing the gas into a first and second portion;

passing the first portion of the gas to step (i) of the process;

treating the second portion of the gas for separation of carbon monoxide contained therein; and passing carbon monoxide separated from the second portion of the synthesis gas to step (iv) of the process.

3. The process of claim 2, wherein the treatment for carbon monoxide recovery comprises membrane separation of the carbon monoxide from the synthesis gas.

4. The process of claim 2, wherein the treatment for carbon monoxide recovery comprises cryogenic separation of the carbon monoxide from the synthesis gas.

5. The process of claim 2, wherein the volume ratio of the first and second portion of the divided synthesis gas stream is between 0.5:1 and 2:1.

* * * * *